(12) United States Patent
Hurson

(10) Patent No.: US 6,711,935 B2
(45) Date of Patent: Mar. 30, 2004

(54) METHOD AND APPARATUS FOR CONTINUOUS MONITORING OF ROAD SURFACE FRICTION

(76) Inventor: James Kevin Hurson, 14 Second St., Orangeville, Ontario (CA), L9W 2B5

( * ) Notice: Subject to any disclaimer, the term of this patent is extended or adjusted under 35 U.S.C. 154(b) by 0 days.

(21) Appl. No.: 09/931,171

(22) Filed: Aug. 17, 2001

(65) Prior Publication Data

US 2002/0124629 A1 Sep. 12, 2002

Related U.S. Application Data

(62) Division of application No. 09/157,567, filed on Sep. 21, 1998, now Pat. No. 6,276,189, which is a continuation-in-part of application No. 08/843,960, filed on Apr. 17, 1997, now abandoned, which is a continuation of application No. 08/403,106, filed on Mar. 13, 1995, now abandoned.

(51) Int. Cl.[7] ............................................. G01N 19/02
(52) U.S. Cl. ............................................................ 73/9
(58) Field of Search ...................................... 73/9, 146

(56) References Cited

U.S. PATENT DOCUMENTS

| | | | |
|---|---|---|---|
| 3,152,468 A | * 10/1964 | Powell ...................... 73/146 X |
| 3,203,500 A | * 8/1965 | Gabserson et al. .......... 180/168 |
| 3,554,024 A | * 1/1971 | Walker ....................... 73/146 X |
| 3,702,205 A | * 11/1972 | Arai et al. ..................... 303/166 |
| 3,811,739 A | * 5/1974 | Nakamura et al. ........... 303/171 |
| 3,893,330 A | 7/1975 | Shute et al. ........................ 73/9 |
| 4,098,111 A | 7/1978 | Hardmark .......................... 73/9 |
| 4,210,019 A | * 7/1980 | Laurent ............................ 73/158 |
| 4,212,063 A | 7/1980 | Hardmark ....................... 73/9 X |
| 4,315,426 A | 2/1982 | Brandon .............................. 73/9 |
| 4,446,522 A | * 5/1984 | Sato et al. ....................... 701/79 |
| 4,545,240 A | 10/1985 | Leiber .......................... 73/146 |
| 4,662,211 A | 5/1987 | Strong .............................. 73/9 |
| 4,779,447 A | 10/1988 | Rath ................................. 73/9 |
| 4,882,693 A | 11/1989 | Yopp ............................ 73/9 X |
| 4,909,073 A | 3/1990 | Takahashi et al. ............. 73/146 |
| 4,958,512 A | 9/1990 | Johnsen ............................ 73/9 |
| 5,056,354 A | 10/1991 | Kuwana et al. ..................... 73/9 |
| 5,109,694 A | 5/1992 | Yahagi et al. ..................... 73/9 |
| 5,113,963 A | 5/1992 | Sigl et al. ....................... 180/97 |
| 5,198,982 A | 3/1993 | Kobayashi ..................... 73/9 X |
| 5,331,839 A | 7/1994 | Schmidt ........................... 73/9 |
| 5,375,452 A | 12/1994 | Helldorfer et al. ................ 73/9 |
| 5,471,384 A | * 11/1995 | Nakashima et al. ........... 701/22 |
| 5,493,893 A | 2/1996 | Kin et al. .......................... 73/9 |

FOREIGN PATENT DOCUMENTS

| | | | |
|---|---|---|---|
| DE | 27 42 110 | 3/1979 | |
| DE | 2841211 | * 4/1980 | .......... G01M/17/00 |
| DE | 153 230 | 12/1981 | |
| DE | 35 43 853 | 6/1987 | |
| FR | 2 656 099 | 6/1991 | |
| FR | 2 660 270 | 10/1991 | |
| GB | 2 243 657 | 11/1991 | |
| GB | 2 279 150 | 12/1994 | |
| WO | 96/28719 | 9/1996 | |

* cited by examiner

*Primary Examiner*—Thomas P. Noland
(74) *Attorney, Agent, or Firm*—Foley & Lardner

(57) ABSTRACT

A method and apparatus for continuously or repeatedly monitoring road surface friction utilizes a separate test wheel attached to a vehicle and in contact with a road surface and a device for detecting slippage of the test wheel resulting from applying either a braking or accelerating torque on the test wheel. A signal corresponding to the applied braking or accelerating torque at the moment slip is detected and used to provide an indication to the driver of the slip condition. The method and apparatus is useful in vehicles as well as aircraft or in other applications where it is desired to monitor road friction. An embodiment of the invention applies and maintains a measured vertical force to the surface of the test wheel of the friction monitor utilizing an electromagnetic force field under processor control. The processor can combine signals from the vertical force torque motor circuit, and the test wheel torque motor circuit.

5 Claims, 8 Drawing Sheets

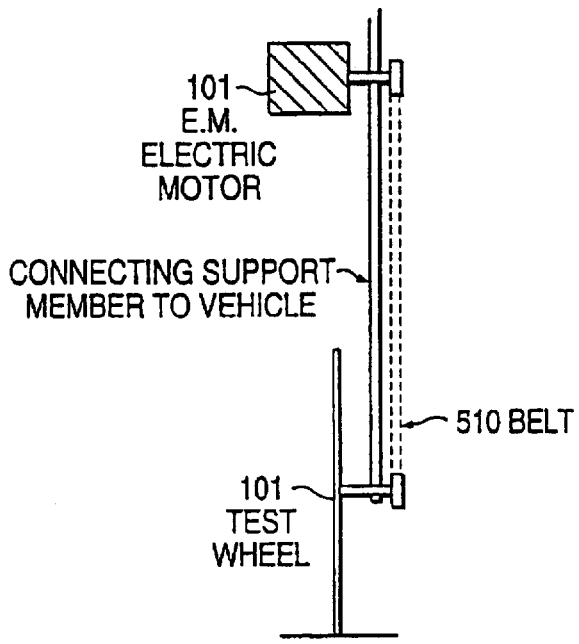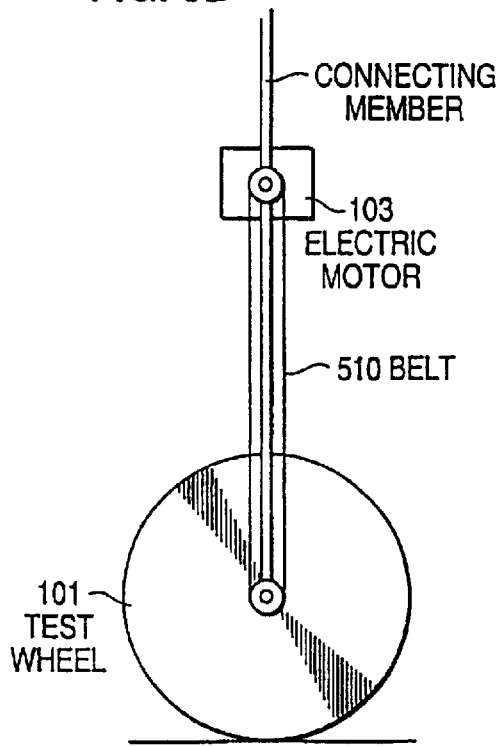

METHOD AND APPARATUS FOR CONTINUOUS MONITORING OF ROAD SURFACE FRICTION

CROSS-REFERENCE TO RELATED APPLICATIONS

This application is a divisional of application Ser. No. 09/157,567, filed Sep. 21, 1998 and now U.S. Pat. No. 6,276,189, which is a continuation in part of application Ser. No. 08/843,960, filed Apr. 17, 1997, now abandoned; which is a continuation of application Ser. No. 08/403,106, filed Mar. 13, 1995, now abandoned.

FIELD OF THE INVENTION

The invention relates to monitoring a road surface condition on which a vehicle is travelling, and more particularly to a method and apparatus for continuously determining a slip condition of a vehicle which is directly related to the coefficient of friction of the road surface.

The invention also relates to a method and apparatus for applying a controlled vertical (i.e., normal) force to a test wheel of a friction monitor and to a friction monitor using such a vertical force monitor in combination with an electromagnetic torque motor for producing slippage of a test wheel.

The invention further relates to a device for monitoring a surface (e.g., road, runway, rail line etc.) condition on which a monitor (e.g., vehicle, airplane, train etc.) is travelling, and more particularly to a method and apparatus for determining a slip condition of a vehicle which is directly related to the coefficient of friction of the road surface while utilizing an electromagnetically controlled vertical force applied to the test wheel.

BACKGROUND OF THE INVENTION

The availability of quantitative information representative of the coeficient of friction of the road surface is very beneficial to drivers of moving vehicles, including planes. An exact knowledge of how slippery the surface is, continuously provided, gives the driver significant advantages in determining safe speeds, distances from other automobiles, acceleration and braking patterns etc. so as to permit a safer operation of the vehicle, plane or apparatus being driven.

Previous devices for monitoring the coefficient of friction had significant disadvantages such as, for example: a failure to provide continuous road friction data over long distances; the use of complex electro-mechanical-hydraulic mechanisms with unfavorable wear characteristics; limited, specificity, variability and responsiveness of test wheel(s) braking force; the use of only indirectly measured values of the force (torque) required to produce slippage; employment of equipment which was unsuited for continuous use close to the ground and in inclement conditions; the use of a cumbersome test wheel suspension and carriage; employment of equipment which produced adverse affect on normal drive operation; and the use of relatively complex designs which produces an expensive apparatus of only limited use.

When measuring the coefficient of friction, various means of applying vertical force have been employed, such as: springs, coils, rubber, compressed air bags, pistons containing air, gases, oil. The foregoing vertical force applying devices have significant limitations. The vertical force tends to increase as tensioning means are compressed and decrease when decompressed. The vertical force is difficult to measure, especially if continuous or frequent measurements are desirable. Further, one is generally not able to standardize the force from one system to another. The vertical force tends to change with use/wear due to deterioration of compressed materials/mechanisms, and to vary with change in temperature and/or moisture.

REVIEW OF PRIOR ART

Several patents are directed to devices which do not employ a separate test wheel but rather employ one of the usual drive or driven wheels of the vehicle. Among these patents are U.S. Pat. No. 4,882,693 to Yopp and U.S. Pat. No. 4,545,240 to Leiber. These devices necessarily adversely effect the driving characteristics of the vehicle.

The Yopp patent measures forces acting on a steering column, such as the steering angle combined with other data.

Other patents teach the use of a test wheel or probe which is lowered into contact with the road surface to perform the desired measurement. Among these patents are U.S. Pat. Nos. 4,098,111 and 4,212,063 to Hardmark; U.S. Pat. No. 4,958,512 to Johnson; U.S. Pat. No. 3,893,330 to Shute; U.S. Pat. No. 4,315,426 to Brandon; U.S. Pat. No. 4,662,211 to Strong; and U.S. Pat. No. 4,909,073 to Takahashi. These patents employ complex devices which are not adapted for continuous operation and wear and which are bulky and complicated in their operation.

OBJECTS OF THE INVENTION

One object of an aspect of the invention is to continuously monitor road surface friction characteristics under a wide variety of road conditions and vehicle velocities.

Another object of the invention is to provide a slippage indication by simulating the actual physical circumstances of slippage of a braked or accelerated wheel of a vehicle.

A further object of the invention is to monitor road surface friction without interfering with the movement of the vehicle wheels or braking system such as would affect the directional path or speed of the vehicle, and in particular, not to affect the freedom of the drive wheels or other wheels of the vehicle or interfere with the braking system, thereby potentially throwing the car off its directional path or causing acceleration or deceleration of the vehicle.

Yet another object of an aspect of the invention is to provide a lightweight, comparatively small monitoring device of suitable weight and size for mounting on an automobile or plane that operates independently of any other system in a moving vehicle, that is comparatively inexpensive to manufacture, and that does not require much maintenance.

Another object of an aspect of the invention is to provide a simple, easily retractable, and easily detachable slip detection device which does not constitute a significant obstacle to the movement of the vehicle.

Another object of an aspect of the invention is to continuously provide near instantaneous, widely variable, highly specific, easily directly measurable, braking or accelerative force; which does not vary, fade, or fail, at any vehicular speed.

Another object of an aspect of the invention is to measure friction conditions without utilizing cumbersome direct mechanical friction devices with their attendant mechanical wear.

Yet another object is to provide a slip detection device suitable for after market mounting on existing vehicles.

It is a further object of an aspect of the invention to provide a compact suspension mechanism for applying and maintaining a controlled, accurately measurable vertical force to the test wheel of a friction monitor, which vertical force is unaffected by variations in temperature, moisture, or atmospheric pressure; remains constant as the test wheel moves up and down with reference to its point of support due to variations in the contour of the measured surfaces; and counters the tendency of the test wheel to move upwards and lose contact with the measured surface. The vertical force may be varied in a controlled manner during use.

SUMMARY OF THE INVENTION

The emphasis with the present invention, in accordance with an aspect thereof, is on the continuous determination of road surface friction characteristics for automobile drivers or pilots, so as to facilitate decision-making with regard to safe travelling speed, braking distance, cornering speed, acceleration speed and the like in various road conditions; wet (hydroplaning), snow, slush, ice, oily surface, etc. Data on varying road coefficient of friction characteristics is continuously presented to the driver as a visual and/or auditory signal.

An embodiment of the present invention provides a means for continuously evaluating the coefficient of friction of the road by providing a relative quantification of the coefficient of friction. The device is comparatively compact and relays to the driver a visual and/or auditory signal indicating relative slipperiness of the road. For example, a suitably placed, non-distracting flashing light could be used; the flashing light can be designed to flash more frequently and more brightly as the slipperiness of the road increases. An audio signal can also be used to inform the driver about road conditions: again, the frequency and intensity of the audio signal can be increased in relation to the slipperiness of the road.

An embodiment of the present invention mimics the strategy commonly used by drivers to evaluate road conditions: pressing on the brake to determine how hard they have to press (decelerative force) in order to produce a limited skid, alternatively, accelerating quickly, to observe how much accelerative force is required to make the drive wheels skid. This device repeatedly and automatically carries out this function. Drivers know that the harder they have to press on their brakes or accelerator in order to produce wheel slippage, the less skiddy the road is. This concept is the basis of the present invention—the more braking resistance or accelerative force required to produce skidding, the greater the coefficient of friction.

The device, through the use of variable resistance or accelerative force, creates slippage of a small test wheel and then detects the earliest sign of skidding of this wheel and measures the amount of force required to produce slippage of the test wheel. In accordance with another aspect of the invention, a processor can combine signals from the circuit regulating the vertical force torque device, with signals from any other circuits, in particular, the circuit to control a torque motor used to produce slippage when measuring a surface (e.g., road, runway, rail line) condition.

An embodiment of the invention utilizes an electromagnetic force field, as distinct from direct mechanical means (springs, air pistons, rubber . . . ) to provide the requisite vertical force acting on the surface of the test wheel.

Information regarding this force is then relayed to the driver. An elementary embodiment of the invention has an open loop control system and a fixed electromagnetic field resistance to the rotation of a test wheel. A warning signal is provided to the driver when the test wheel skids indicating that the road surface has reached a potentially hazardous threshold.

Another embodiment of the invention utilizes an open-loop control system and a variable braking resistance. A series of predetermined resistance levels are applied, and the test wheel slip condition is conveyed to the driver at each state, providing a more refined indication of road slipperiness.

Another embodiment of the invention utilizes a closed feedback loop control system with variable braking resistance or accelerative force. The test wheel is first allowed to rotate freely as the vehicle travels. A timer initiates the test process, and variable resistance (or accelerative force) is applied to the test wheel using, for example, an electric motor, designed to produce torque in the same or opposite direction (or same direction in the case of acceleration) to the rotation of the test wheel. The braking resistance or accelerative force is increased until the test wheel slips. A sensor determines the rotational speed of the test wheel and, from this test wheel rotational speed in any given period of time, the amount of slip of the test wheel is determined. The amount of braking resistance or accelerative force required to generate wheel slip is measured, and this information is conveyed to the driver by various display methods. The variable braking or accelerative force is then decreased and the process is repeated.

Another embodiment of the invention employs a second or reference wheel. This reference wheel has no brake and serves solely as a reference tachometer to facilitate determination of the percentage slip of the braked or accelerated test wheel. Optionally this reference wheel can power a generator, which, generator can provide E.M.F. to the electric motor and/or battery.

A test wheel is used, as opposed to actual vehicle wheels, to ensure that the repeated road surface monitoring does not affect normal vehicle operation. The test wheel is designed to be easily retractable and instantly detachable to minimize the effects of roadway obstacles. The desire for simplicity and low cost leads to a method that uses increasing braking resistance or accelerative force to induce slip instead of a geared test wheel driven at a predetermined slip, and that monitors road surface conditions to produce a relative quantification of the actual coefficient of friction. Similarly, variable resistance to rotation of the test wheel is provided by an electric motor, instead of cumbersome mechanical brakes.

Another embodiment of the invention is directed to a method of and apparatus for applying and maintaining a vertical force, which may be variable if desired, to a test wheel of a friction monitor utilizing an electric torque device, such as a motor, under control of an electronic processor such as a digital computer or the like.

BRIEF DESCRIPTION OF THE DRAWINGS

FIGS. 8A and 8B illustrate yet another embodiment of the invention for connecting an electric motor to a test wheel of the invention;

DETAILED DESCRIPTION OF THE PREFERRED EMBODIMENTS

The present invention is concerned with the determination of a relative variation in the coefficient-of friction within a range affecting safe operation of a moving vehicle by use of an arbitrary standard. This arbitrary standard refers to the pre-determined constant downward pressure (vertical force) on the test wheel, exerted through the suspension connecting member between the monitoring device itself and the vehicle to which it is attached, the standard width and contour of the test wheel, and the standardized coefficient of friction of the test wheel surface. Such a relative quantification provides for meaningful quantitative differentiation of the coefficient of friction on the road surface. Vertical force sensor (154) where indicated, continuously monitors the vertical force, and signals from this monitor are continuously provided to the central processor.

Figure 1:
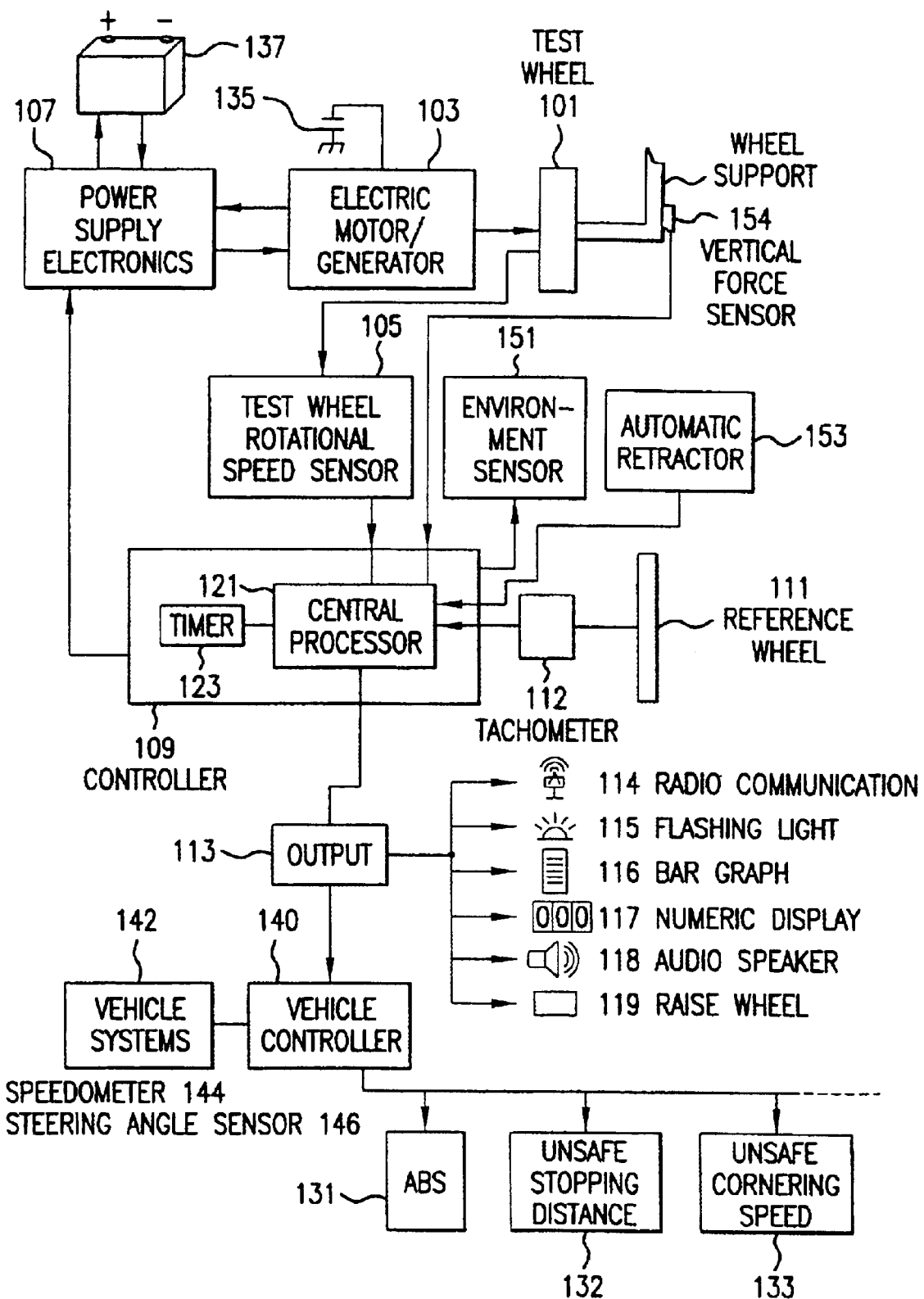
FIG. 1 is a block diagram of the road surface friction monitor.

FIG. 1 shows an overall block diagram of the friction monitoring system. The system comprises a test wheel 101, electric motor 103, test wheel rotation speed sensor 105, power supply electronics 107, controller 109, and output 113. The monitoring device may include vertical force sensor 154 for measuring the vertical force on the test wheel and feeding a signal indicative thereof to the controller. The controller 109 includes a central processor 121 (i.e., a microprocessor) and a timer 123. The test wheel 101 is in contact with the ground and accordingly rotates in the same direction as the wheels of the vehicle. The timer 123 (which may be a software timer configured within the central processor 121) periodically/repeatedly initiates the test sequence. The time interval between test sequences is variable, and is typically milliseconds to tenths of seconds.

Energy is supplied from the power supply electronics 107, under the periodic direction of the timer 123 and controller 109, to the electric motor 103. The electric motor 103 is designed to produce torque in the opposite direction from which the test wheel 101 rotates, creating a braking resistance on the test wheel 101, or the same direction producing an accelerative thrust. The central processor 121 increases the EMF to the electric motor 103 via the power supply electronics 107, creating a corresponding increase in the braking resistance or accelerative force until the central processor 121 detects slippage of the test wheel 101, measures, then reduces the EMF provided to the electric motor 103 via power supply electronics 107, decreasing the braking resistance or accelerative force, and the test wheel 101 is free to rotate in conjunction with the surface of the road until the next test cycle initiated by the timer 123. The rotational speed of the test wheel 101 is measured by the test wheel rotational speed sensor 105 and a test wheel speed signal is conveyed to the central processor 121. Signals from vertical force sensor (154) are also conveyed to the central processor.

Optionally, a second free-wheeling wheel 111 which has the same diameter as the test wheel and which is not impeded by an applied resistance is used as a reference/comparison tachometer. This reference wheel tachometer is free to rotate as the vehicle moves, the only resistance being created by its own bearings. A reference wheel rotational speed sensor 112 measures the speed of the reference wheel 111, and supplies a reference speed signal to the central processor 121. Alternatively, a signal from the vehicle speedometer may be used to provide the reference signal.

Where a reference wheel is deployed, the rotational speed differential between the test wheel 101 and the reference wheel 111 provides a more precise indication of the extent of slippage of the test wheel 101, which can be expressed as a percentage, greater or lesser, than the reference wheel and provides the basis for the central processor 121 to detect whether the test wheel 101 has slipped.

The central processor 121 is programmed to determine that a slip condition (a first instance of a slip condition i.e. slippage up to one hundred percent, greater or lesser, than a reference wheel) is occurring, its percentage slip, greater or lesser than the reference wheel, and continuously measures the EMF required to produce any given percentage slip. Slip curves graphically demonstrate coordinates of braking torque (vertical axis) and percentage slip (horizontal axis); maximum torque in relation to percentage slip, usually in the 10 to 20% range.

The torque, braking or accelerative, required to cause slippage of the test wheel will vary according to the degree of slip of the test wheel. Degree of slip can be expressed as a percentage increase or decrease, in test wheel rotational speed, compared to a reference tachometer wheel. A braked, totally locked, non-rotating wheel corresponds to one hundred percent slip. For purposes of computing representative data on the coefficient of friction, it is valuable to determine the relationship between the percentage slip and the torque required to produce it. If the test wheel 101 is rotating through snow, the snow tends to slow down the test wheel 101, and this "roll resistance" is reflected in the amount of energy required to accelerate or brake the test wheel 101. According to the invention, varying degrees of slip, from braking or accelerating force, can be created and correlated with the electric power (voltage supplied to the motor 103) required to create such varying degrees of slip, taking into account roll resistance and other physical factors that affect braking. Braking torque is proportional to voltage supplied to the motor 103. Tabulations of the braking torque in known varying slip conditions, as a function of any degree of slip, at any given test wheel speed, may be stored in a memory of the central processor 121, which data can be combined with EMF torque detection signal, and/or other signals, for further refinement of friction characteristics. Accordingly, the central processor 121 is programmed to measure the voltage going to the electric motor 103 at any given percentage slip (coordinate on the slip curve) up to a maximum designated percentage slip, then after measuring this voltage to decrease the voltage to the electric motor 103, decreasing braking or accelerative forces acting on test wheel 101 and initiating another test cycle. Processor 121 can also be programmed to maintain percentage slip of the test wheel 101, so as to maximize the data available on the coefficient of friction of the road. In general, the central processor 121 may be programmed to use any electrical property of the torque motor to calculate the slip condition such as voltage, phase, current, power or the like.

The measure of EMF at which slip of the test wheel 101 occurred is transferred from the central processor 121 via an EMF torque detection signal to output block 113. The measured EMF is related to the slipperiness of the road, and the output block 113 conveys this road surface condition information to the driver in any number of methods, for instance as a flashing warning light 115 or audio warning signal 118 previously described herein, or as a bar graph 116 or numeric display 117. The skilled artisan will recognize that such information could be delivered to the driver instantly and/or as an averaged value, for example a twenty foot average of road conditions. When the friction monitor is used in conjunction with aircraft, the output block 113 could be coupled to a radio communication device 114 that directly transmits runway surface condition information to the control tower. In such a case, aircraft taxing down the runway or taking off or landing on the runway can transmit a detailed road surface condition (i.e., coefficient of friction condition) map of the runway condition along its route. This information can be very valuable to air traffic controllers in controlling other aircraft in queue to land or take off.

The output indication could also be a driver prompt (visual and/or audible) 119 that indicates to the driver that the coefficient of friction of the road is high enough to be above the threshold of concern and this would prompt the driver to turn off the system and elevate the test wheel 101.

Alternatively, or additionally according to the invention, the information on slipperiness can be provided to a vehicle control system 140. The vehicle control system 140 may be a controller having a microprocessor for combining the road surface information with data from other vehicle systems 142 to facilitate safe vehicle operation. For instance, the vehicle systems 142 may be a speedometer or a steering angle sensor, and the vehicle control system 140 could operate in cooperation with an anti-lock brake system 131 or generate warning signals such as an unsafe stopping distance signal 132, an unsafe cornering speed signal 133, etc. The skilled artisan will recognize that the vehicle systems 142 and safety features 131, 132, 133 are by way of example and not by way of limitation.

FIG. 1 shows that the electric motor 103 can also function as a generator, and that a capacitor 135 can be attached to the motor/generator 103 to provide bursts of energy used to brake or accelerate the test wheel 101. The electric motor/generator 103 may also provide energy to the battery 137 so as to facilitate its operation.

Figure 2:
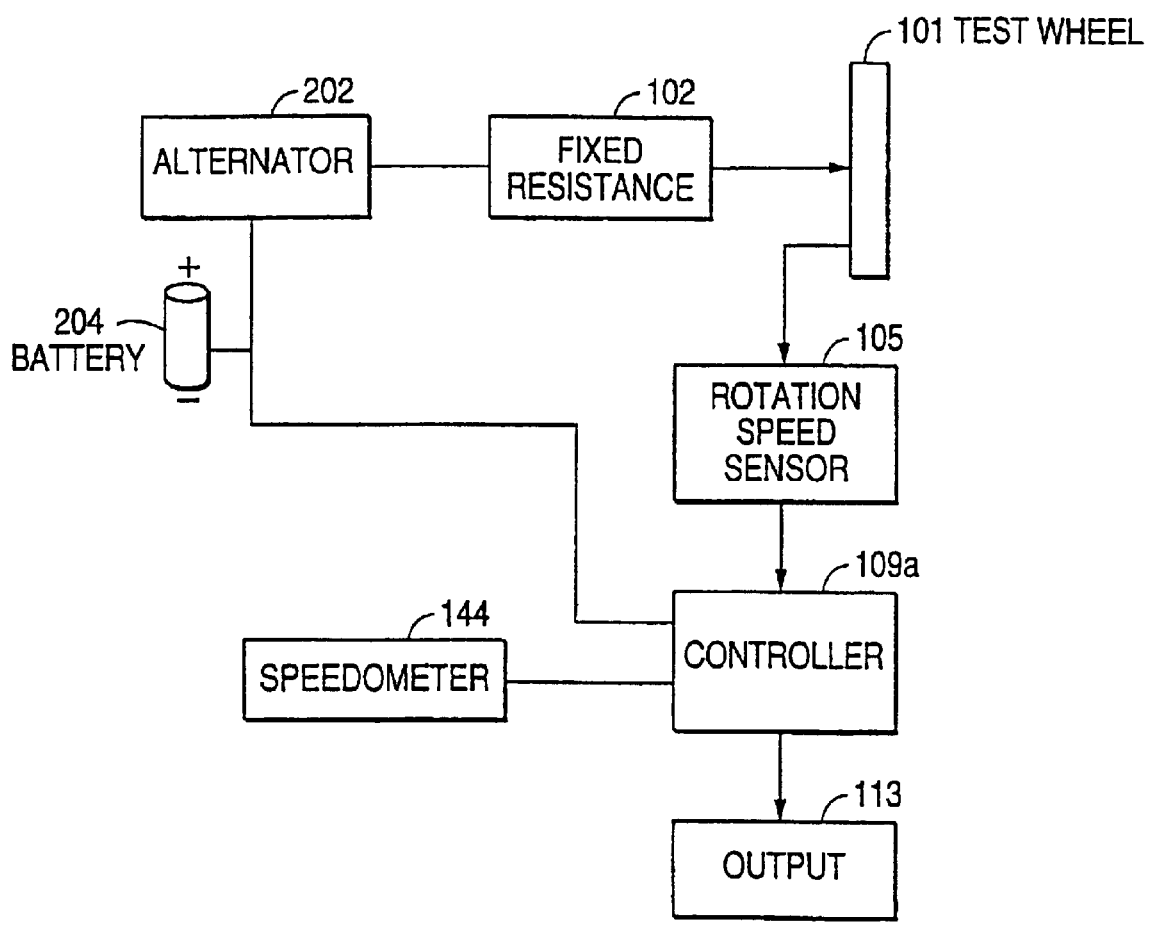
FIG. 2 is a block diagram of an elementary embodiment of the invention.

FIG. 2 shows an embodiment of the invention in its most elementary form, consisting of test wheel 101, test wheel rotation speed sensor 105, a fixed (i.e., constant) electromagnetic or other resistance device 102 and controller 109*a* connected to output 113. In this "open loop" embodiment, there is a no feedback from the controller 109*a* to alter the strength of the resistance device 102. An on/off function is provided, in that if the coefficient of friction on the ground is sufficient to keep test wheel 101 rotating while fixed resistance device 102 acts to resist this rotation, then one signal is provided to the driver of the vehicle; conversely, if the conditions change and the coefficient of friction beneath test wheel 101 is not sufficient to maintain its grip on the wheel when resistance device 102 is active, and therefore the test wheel 101 slips, then a different signal is provided to the driver. There are no means for variable resistance in this embodiment. The driver is provided with a statement that a certain road surface friction threshold has been exceeded, but no quantification beyond this level is provided. Fixed resistance could be provided by an electric motor or permanent magnets in place of the coils in the electric motor. As described previously herein, a timer 123 within controller 109*a* periodically initiates test cycles to provide continuous monitoring of road surface conditions.

According to the invention, the fixed resistance of 102 can be combined with an alternator 202 to produce energy for the electrical system of this device, including a signalling system represented by output 113. A small battery 204 can also be incorporated to provide power when the generating function is limited, such as when there is very slow movement of the vehicle. This self-powering, more elementary system of FIG. 2 is less expensive to produce and easier to install than the embodiment of FIG. 1. Moreover, the embodiment of FIG. 2 is more easily retrofitted to existing vehicles, aircrafts and the like.

Figure 3:
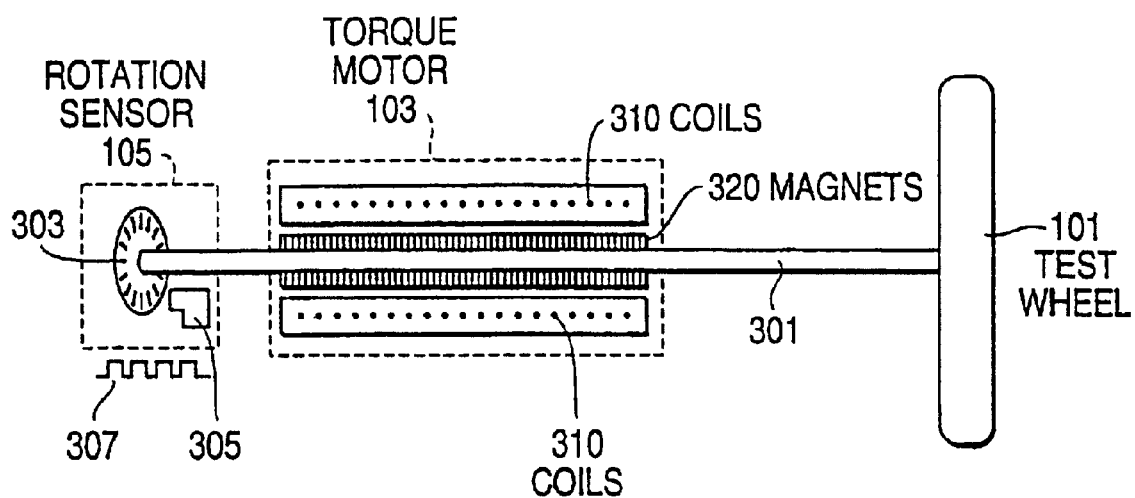
FIG. 3 illustrates the electric motor and rotation sensor according to the invention.

This alternative embodiment of FIG. 2 is also simple and inexpensive in that it does not utilize the reference wheel tachometer 111 of FIG. 1. One method to detect slip uses signals from the vehicle speedometer 144 to the controller 109*a* as a reference signal. Alternatively, slip is detected by the controller 109*a* without such a comparison signal. The slip of the test wheel is detected by an analysis of the number of signals in any given period of time from the test wheel rotational speed sensor 105. FIG. 3 shows an embodiment of the test wheel rotation speed sensor 105. Pulses 307 are generated when markers 303 on rotating shaft 301 pass in front of a scanner 305. For example, the test wheel rotation speed sensor 105 could be a magnetic or optical detecting device.

FIG. 3 also shows the motor 103 consisting of coils 310 and magnets 320. The magnets are shown fixed to the rotating shaft 301 and the coils 310 are fixed to the motor housing. A variable resistor is achieved by varying the voltage to the coils 310.

Optionally, as indicated above, the coils 310 may be replaced by permanent magnets to provide a fixed resistance. Incidentally, when a variable resistance is desired, as in the embodiment of FIG. 1, the variable resistance is achieved by varying the voltage to the coils 310 as controlled by central processor 121.

In the embodiment of FIG. 2, the number of pulses 307 over a given interval of time (the frequency) represent the rotational speed of the test wheel 101. When the test wheel is accelerated or braked, an increase or decrease in pulses 307 in a given period of time disproportionate to vehicle speed indicates that the test wheel 101 is slipping. For example, where the test wheel is braked, if a frequency of pulses corresponding to a test wheel velocity of 25 mph suddenly changes to a frequency of pulses corresponding to 5 mph, and this change occurs in a time period shorter than that needed for the vehicle to decelerate by this amount, then the test wheel 101 has slipped. A proportional, rather than absolute, decrease or increase (when accelerated) in test wheel velocity is used to detect slippage. For example, assuming constant or near-constant (i.e., slowly changing) velocities, a one-third decrease or increase in the number of signals from the test wheel rotational speed sensor 105 in any given fraction of a second could be evidence of slip as distinct from deceleration or acceleration associated with the more gradual slowing or speeding up of the vehicle itself.

In another open-loop embodiment of the invention, variable braking resistance from the electric motor 103 is applied to the test wheel 101, although there is no feedback control to the electric motor 103 from the controller 109*a*. The applied variable braking resistance does not depend on the slip condition of the test wheel 101. According to the invention, a plurality of predetermined and increasing braking resistances are consecutively applied to the test wheel 101, and the slip condition is measured at each of the braking resistance levels. For example, if five braking levels are used, the test begins with the electric motor 103 applying the first braking level and the controller 109*a* detecting whether the test wheel 101 slips; then the second braking level is applied and the presence of slip detected; then the third, fourth, and fifth braking levels are applied in order, and the presence of slip is detected for each braking level. Since the system is open-looped, the five (for example) braking levels are applied regardless of the outcome of the slip from a previous braking level. However, the driver is alerted to the existence of slip as soon as it is detected through output 113 and indicators as shown in FIG. 1. Further, a quantification of the road surface friction may be displayed, if desired, by correlating the braking level at which slip first occurred with the braking level for wheel lock which represents 100% slip condition. This test method provides a finer quantification of road surface conditions than the fixed resistance method previously described herein, while avoiding the complexity of a closed-loop feedback system. At each fixed level of resistance, the slip condition can be determined from a sudden change in the number of pulses 307 inconsistent with a vehicle deceleration condition. Similarly predetermined accelerative torque is applied to the test wheel.

Figure 4:
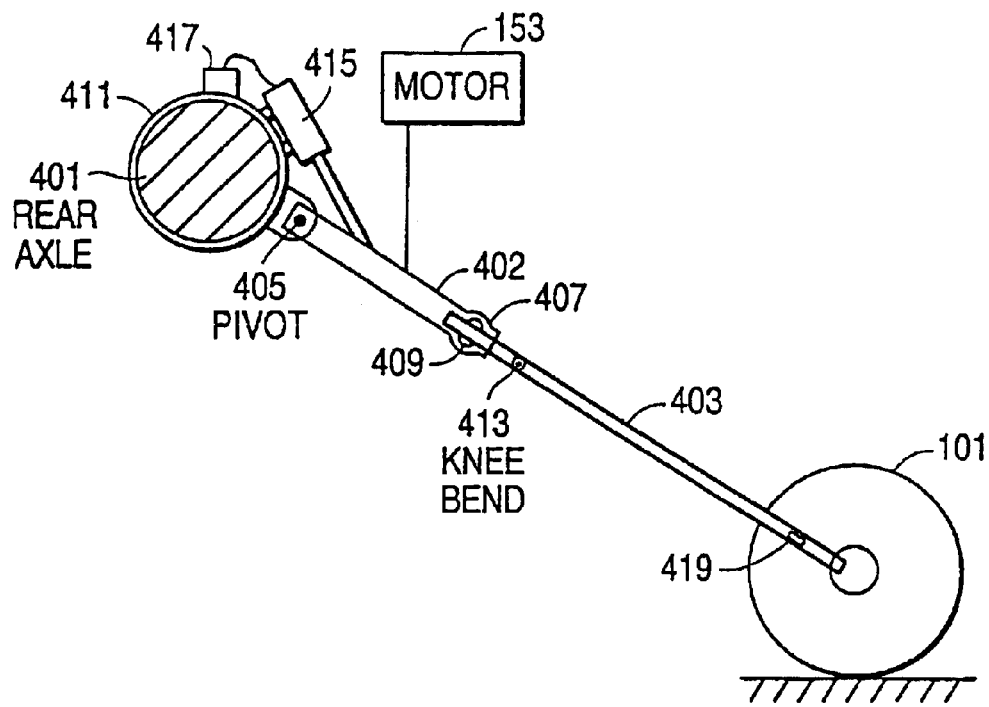
FIG. 4 illustrates a side view of the friction monitor.

FIG. 4 shows a side view of the friction monitor. Connecting member 402 is shown attached to rear axle 401 of an automobile. Member 402 can be attached to any part of the vehicle, including the body. Preferably, member 402 is attached to the underside of the vehicle for ease of operation. The test wheel 101 rotates in the same direction as the vehicle wheels when the vehicle is moving forward. The test wheel 101 can, if desired, be placed close to the track created by the wheels of the vehicle. It is in contact with the ground while in operation and can be lifted up by rotation about pivot 405 either manually or mechanically when not needed. A hook or latch is fixed to the vehicle frame and used to secure the wheel in a retracted (non-operational) position. FIG. 1 shows that an environment sensor 151 and automatic retracting means 153 (such as a motor) can be connected to the controller 109 to automatically elevate the test wheel 101. The environment sensor 151 could be a moisture sensor, a temperature sensor, a device for measuring the reflectance of the road (used to detect ice), etc., and, when the sensor 151 indicates there is no need for road surface friction monitoring, the controller 109 automatically retracts the test wheel 101.

Another feature according to the invention is a detaching capability. The detaching means 407 allows member 403 to be instantly detachable from member 402 if the test wheel 101 becomes caught on an object during vehicle movement. This detaching capability may be provided by, for instance, spring mounted restraints 409, similar to those found in an umbrella telescoping support arm. The power lines for electric motor 103 and signal lines from the controller 109 are coupled through a quick disconnect device which pulls apart when a "jerking" force above a certain threshold is applied.

Figure 5A:
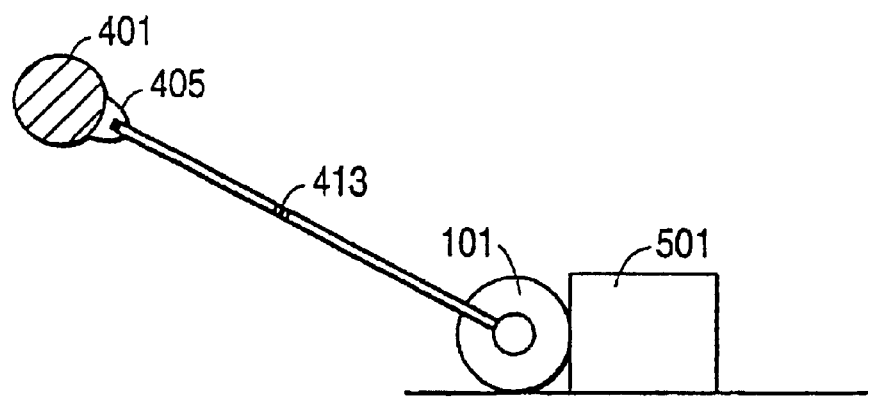
FIGS. 5A, 5B, and 5C illustrate the folding mechanism of the friction monitor.
Figure 5B:
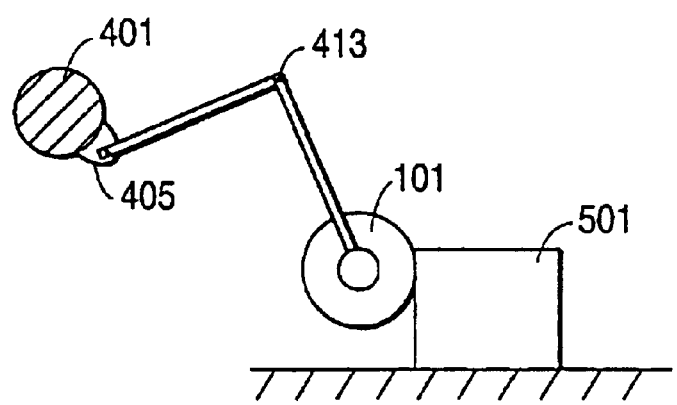
Figure 5C:
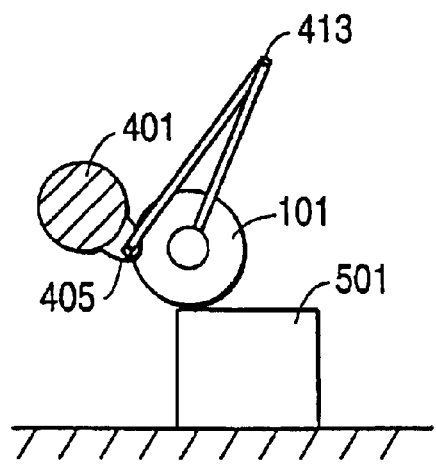

Another feature to the invention is a folding mechanism that operates when fixed objects encounter the test wheel 101 from the rear. As shown in FIG. 5A, an obstacle 501 may encounter the test wheel 101 from the rear and jam the test wheel assembly. This may occur, for instance, when the vehicle moves in "reverse" and encounters a fixed object. As shown in FIGS. 5A and 5B, the joints at pivot 405 and knee bend 413 allow the assembly to fold upwards and the vehicle to pass safely over the obstacle 501.

Figure 6:
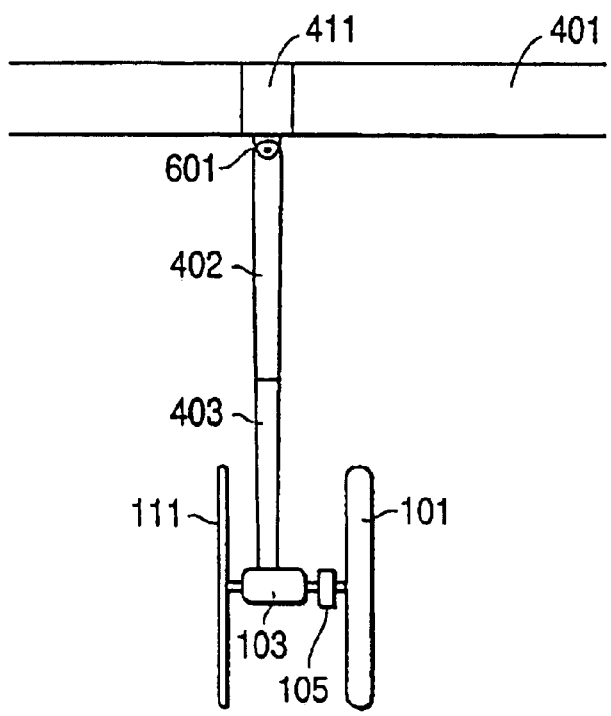
FIG. 6 shows a plan view of the friction monitor.

A mechanism is also provided as part of the suspension system to allow for movement of the test wheel 101, motor 103 and associated controls in any direction so as to minimize the possibility of damage to the measuring unit. As an example of such a suspension mechanism 601, FIG. 6 shows a plan view of one possible configuration of the friction monitoring device according to an embodiment of the invention. Mounting bracket 411 may be placed anywhere along the rear axle 401, such that the test wheel 101 may be located near the center of the vehicle or very near to one of the vehicle tires. Note that the reference wheel 111 is much thinner than the test wheel 101, so that the majority of the vertical force on the test wheel assembly rests on the test wheel 101. Furthermore, the outer perimeter of the reference wheel 111 is made of soft material such that a greater percentage of the vertical force on the assembly is brought to bear on the test wheel 101. Test wheel 101 can be made in such a way as to minimize its mass in order to reduce its momentum and its effect on vehicle stability.

A constant vertical force of the test wheel 101 against the ground is desirable to standardize measurements of the road surface condition, so that the same measured value means the same thing to the driver of a truck as it does to the driver of a small car. This near constant vertical force is provided by the suspension means 415 and members 402 and 403 of FIG. 4. The suspension means 415 can be, for instance, a deformable elastic material such as silicone, rubber, coil, spring, compressed air, etc., and is constructed so that the vertical force of the test wheel 101 on the ground varies little with upward or downward movement of the vehicle in relation to the ground. Thus, a near uniform vertical force is maintained when the vehicle passes over bumps or potholes in the road. The suspension means 415 is calibrated at the time of installation of the test wheel 101, and further standardization is achieved by making the test wheel width, surface contour, and surface coefficient of friction the same for all units. Furthermore, the wear characteristics of the test wheel 101 can be designed so that the surface of the wheel has a constant coefficient of friction. An adjusting means 417 to alter the spring-like resistance intermittently or continuously can also be incorporated. For example, if compressed air is used in the suspension means, the adjusting means 417 may increase (via a compressed air reservoir) or decrease the pressure therein.

Spring-like suspension between the surface of the test wheel and the point at which the friction monitor is mounted on the vehicle can also be achieved by making the connecting members 402, 403 between the electric motor and the vehicle of flexible spring-like material.

According to an aspect of the invention, the vertical force sensor 154 (FIG. 1), in the form of a strain gauge 419, can be juxtaposed with the axle of test wheel 101 to continuously measure the vertical force on the test wheel 101 as shown in FIG. 4. Since the coefficient of friction is a function of the vertical force on the test wheel 101 and the amount of torque required to brake or accelerate it, mathematical manipulation of the friction value quantification is continuously carried out to take into account the variations in the vertical force on the test wheel 101. By accounting for such variations in the vertical force, the accuracy of the monitor is increased.

Figure 7:
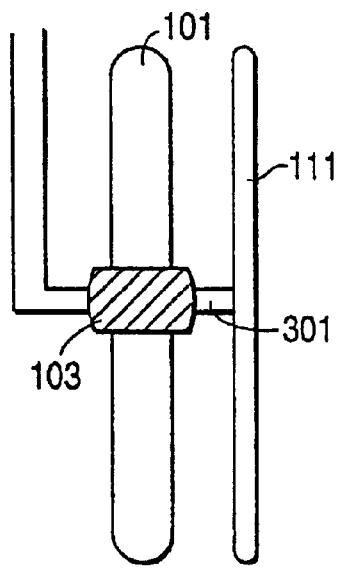
FIG. 7 shows an alternate configuration of the friction monitor.

FIG. 7 shows an alternative physical configuration for the friction monitor. The electric motor 103 is placed in the hub of the test wheel 101 to facilitate operation under inclement conditions, such as by preventing moisture from contacting the motor, etc. Note also that, according to the invention, the reference wheel 111 can be placed at any location along the axle 301.

FIGS. 8A and 8B show an alternative physical configuration for the friction monitor. The electric motor 103 is placed closer to the point of attachment of the monitor to the vehicle and works in co-operation with the test wheel by means such as an enclosed belt drive 510.

The width of the surface of the test wheel can be as narrow as a blade. A narrower surface requires less torque to cause slippage and less vertical force to maintain representative contact with the surface. The test wheel diameter can be a mere fraction of what is shown.

In an alternative physical configuration for the friction monitor, the electric motor is placed closer to the point of attachment of the monitor to the vehicle and works in co-operation with the test wheel by means such as an enclosed belt drive.

Figure 9:
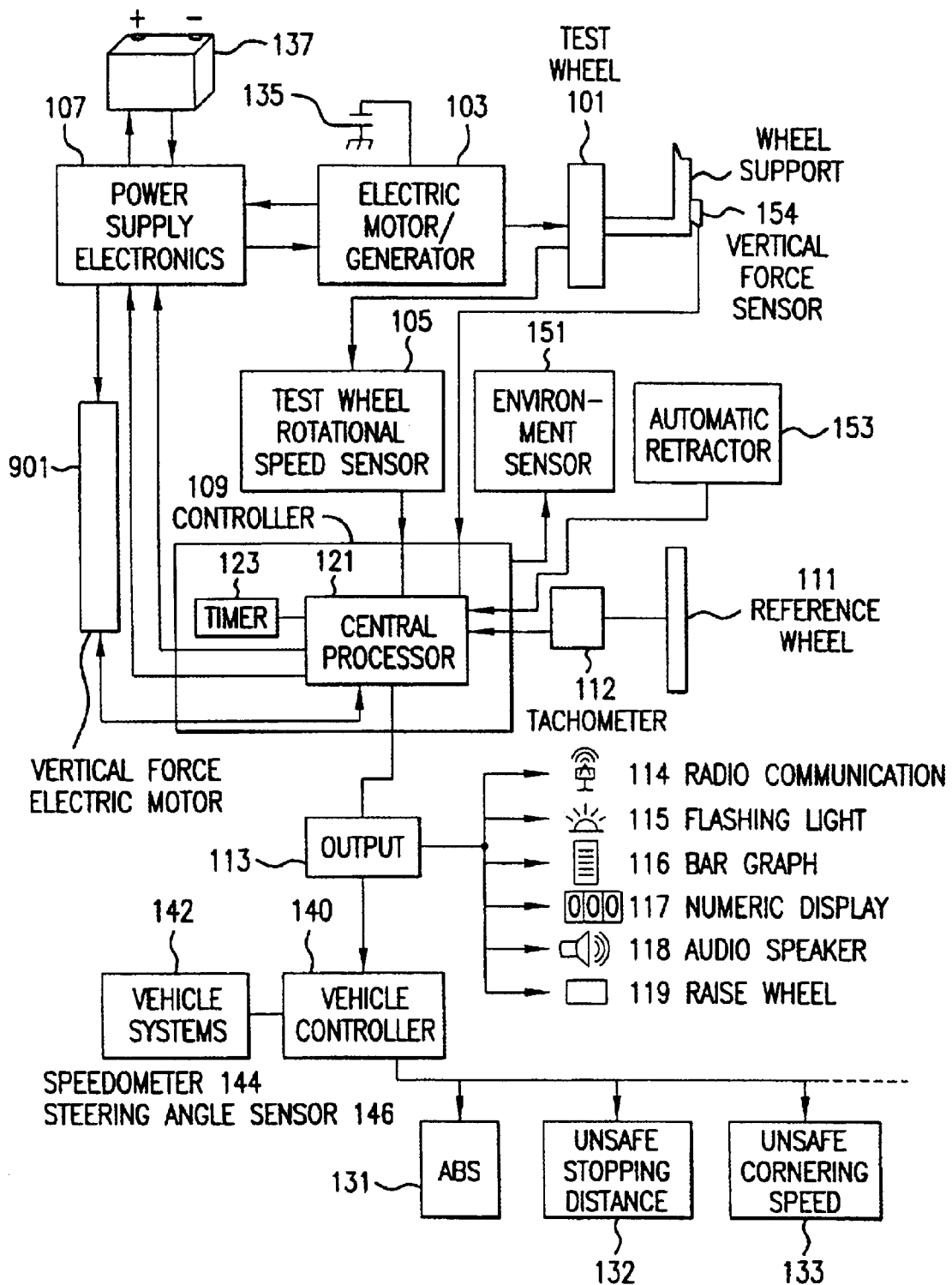
FIG. 9 is a block diagram of electromagnetic vertical (normal) force torque motor in combination with the friction monitor.

FIG. 9 shows an overall block diagram of the electromagnetic suspension and the friction monitor in which a vertical force electric torque motor 901 is controlled by central processor 121. This embodiment is an improvement over the vertical force structures described in relation to FIG. 4. In effect, in FIG. 9, the electric motor 901 replaces element 415 of FIG. 4 to provide a more controllable vertical force applying mechanism. Electric motor 901 can be used effectively even without a vertical force sensor 154 since, like the slip torque motor 103, the voltage or other electrical characteristic of motor 901 can be used by the central processor 121 as a measure of the vertical force and thus used in the determination of the calculation for the road surface condition. Of course, vertical force sensor 154 may also be used in the embodiment of FIG. 9 for either calibration proposes or as an added input for improved accuracy of the system. The motor 901 is connected for applying the requisite vertical force as shown in greater detail in FIGS. 10 and 11.

While the term "vertical" force is generally used herein, it is understood that the coefficient of friction is calculated using the force, or component of force, normal to the surface, so that a more accurate term is a normal force. In most applications, the normal force will be in the vertical direction where the surface, such as a roadway/runway, is horizontal.

In FIG. 9, the central processor quantifies the coefficient of friction utilizing signals representative of the vertical force applied to the surface of the test wheel, and the torquing force required to produce a given degree of slip of the test wheel. The central processor can vary the vertical force applied to the test wheel and/or torquing force to the test wheel (to produce slippage), in any given interval, in any sequence, and at any rotational speed of the test wheel, to maximize data on road friction characteristics.

Figure 10:
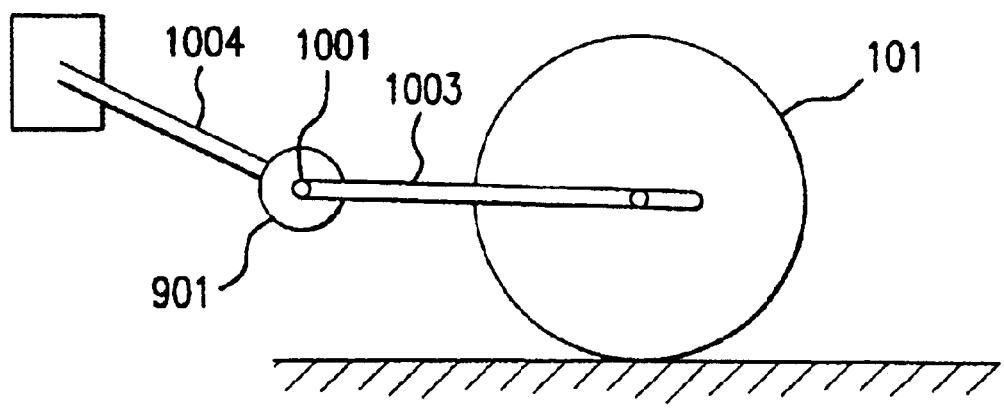
FIG. 10 illustrates the suspension mechanism for the test wheel, comprising a pivot with an electric torque motor adjacent to the test wheel.

FIG. 10 illustrates the test wheel 101, with support member 1003 attached to the axle of the test wheel 101 and pivotally attached to a support member 1004. The casing of torque motor of 901 is attached to a fixed point of support by member 1004 and the armature of the torque motor is attached to support member 1003. Pivot 1001 can advantageously be placed at the same height above the measured surface as the axle of test wheel 101. Support member 1004 may be pivotally attached to its point of attachment with electromagnetic solenoid attachment and detachment means, to facilitate release. Test wheel 101 can be elevated by reversing polarity to torque motor 101.

Figure 11:
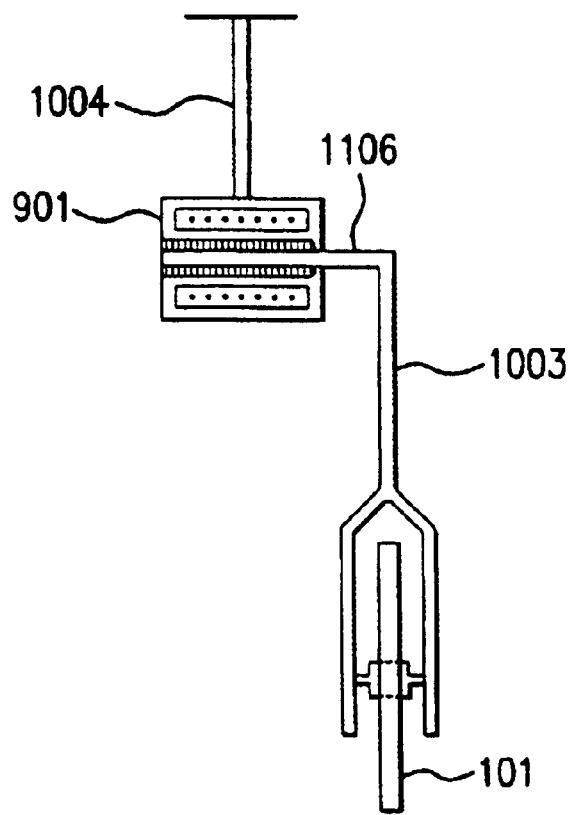
FIG. 11 illustrates in greater detail the pivot with the electric motor adjacent to the test wheel.

FIG. 11 shows the torque motor 901 with its casing attached to support member 1004 and armature 1106 attached to or integral with support member 1003.

While the invention has been described in terms of the embodiments illustrated, it will be appreciate by one of skill in the art that various modifications and improvements may be made within the spirit of the invention as defined by the appended claims. For example, while an electric torque motor is advantageously deployed to produce the vertical force, it will be appreciated by one of skill in the art, taking into account known methods of creating electromagnetic force fields, that a solenoid may alternatively be used instead of the torque motor, especially where applications require only small displacements of the test wheel.

What is claimed is:

1. An apparatus for use with a vehicle for repeatedly measuring road surface conditions, comprising:

a test wheel, separate from the vehicle wheels, attached to said vehicle and positioned for contact with a road surface, so as to rotate due to contact with said road surface upon movement of said vehicle;

means for applying a variable electromagnetic field torque opposing rotation of said test wheel, so as to produce slippage of said test wheel;

means for measuring an amount of voltage utilized in said electromagnetic field applying means and for providing a voltage measurement signal corresponding thereto;

means for measuring a rotation speed of said test wheel and generating a test wheel rotation speed signal;

a controller connected to receive said test wheel rotation speed signal and said voltage measurement signal, said controller generating an output signal in response to a slip condition of said test wheel based on said test wheel rotation speed signal and said voltage measurement signal, and means for providing an indication of said output signal.

2. The apparatus as claimed in claim 1, further comprising:

means for generating a reference signal indicative of the speed of said vehicle, wherein said controller is connected to receive said reference signal and generates said output signal in response to said test wheel rotation speed signal and said reference signal.

3. The apparatus as claimed in claim 1, wherein said variable torque applying means is connected to receive said output signal and varies the magnitude of said variable torque in response thereto.

4. An apparatus, for use with a vehicle having wheels, for repeatedly measuring road surface conditions, comprising:

a test wheel, separate from the vehicle wheels, attached to the vehicle and positioned for contact with a road surface so as to rotate upon movement of the vehicle;

means for applying a variable, electromagnetic field, accelerative torque to produce slippage of said test wheel;

means for measuring an amount of voltage utilized in applying said accelerative torque and for providing a voltage measurement signal corresponding thereto;

means for measuring a rotation speed of said test wheel and generating a test wheel rotation speed signal;

a controller connected to receive said test wheel rotation speed signal and said voltage measurement signal, said controller generating an output signal in response to a slip condition of said test wheel based on said test wheel rotation speed signal and said voltage measurement signal; and means for providing an indication of said output signal.

5. The apparatus as claimed in claim 4, further comprising:

means for continuously producing a vertical force test signal representative of the vertical force acting on said test wheel, and wherein said controller is further responsive to said vertical force test signal to produce said output signal.

* * * * *